(12) United States Patent
Toyoda

(10) Patent No.: US 8,467,062 B2
(45) Date of Patent: Jun. 18, 2013

(54) INSPECTION DEVICE AND PRODUCING METHOD OF WIRED CIRCUIT BOARD

(75) Inventor: Yoshihiro Toyoda, Osaka (JP)

(73) Assignee: Nitto Denko Corporation, Osaka (JP)

( * ) Notice: Subject to any disclaimer, the term of this patent is extended or adjusted under 35 U.S.C. 154(b) by 55 days.

(21) Appl. No.: 13/137,399

(22) Filed: Aug. 11, 2011

(65) Prior Publication Data

US 2012/0069339 A1    Mar. 22, 2012

(30) Foreign Application Priority Data

Sep. 16, 2010    (JP) ................................. 2010-207563

(51) Int. Cl.
*G01N 21/00*    (2006.01)
(52) U.S. Cl.
USPC ........................................................ 356/432
(58) Field of Classification Search
USPC ........................................................ 356/432
See application file for complete search history.

(56) References Cited

U.S. PATENT DOCUMENTS

| 2007/0121108 A1* | 5/2007 | Ishimaru et al. ........... 356/237.2 |
| 2007/0146697 A1* | 6/2007 | Noguchi et al. ........... 356/237.5 |

FOREIGN PATENT DOCUMENTS

JP          2007-042956       2/2007

* cited by examiner

*Primary Examiner* — Tu Nguyen
(74) *Attorney, Agent, or Firm* — Jean C. Edwards, Esq.; Edwards Neils

(57) ABSTRACT

An inspection device includes a light emitting unit emitting incident light that enters the insulating cover layer and a light receiving unit receiving reflected light that is reflected from the incident light on the surface of the insulating cover layer. The light emitting unit includes a first light emitting portion in a ring state that emits the incident light so that the angle thereof with respect to the surface of the insulating base layer is in the range of 25° or less and a second light emitting portion in a ring state that emits the incident light so that the angle thereof with respect to the surface of the insulating base layer is in the range of 35 to 65°.

6 Claims, 10 Drawing Sheets

FIG.3
(a)
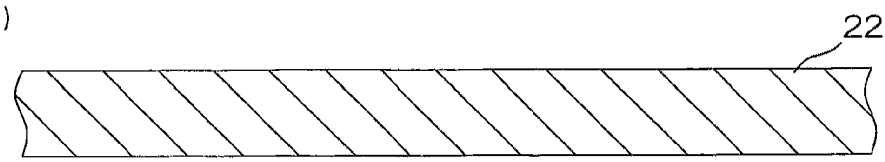
(b)
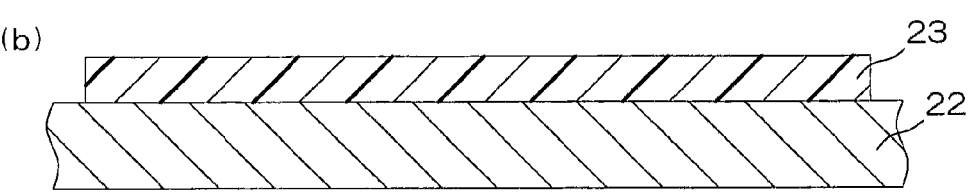
(c)
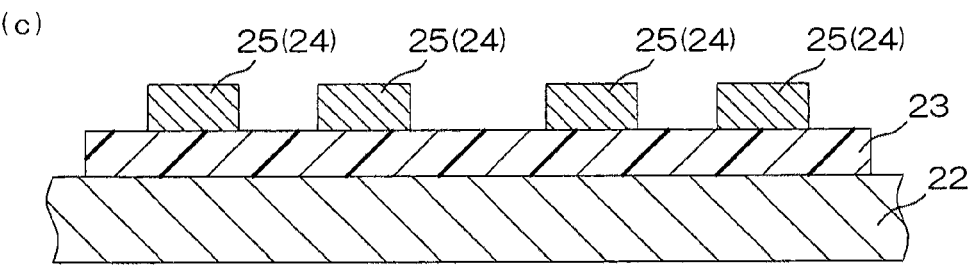
(d)
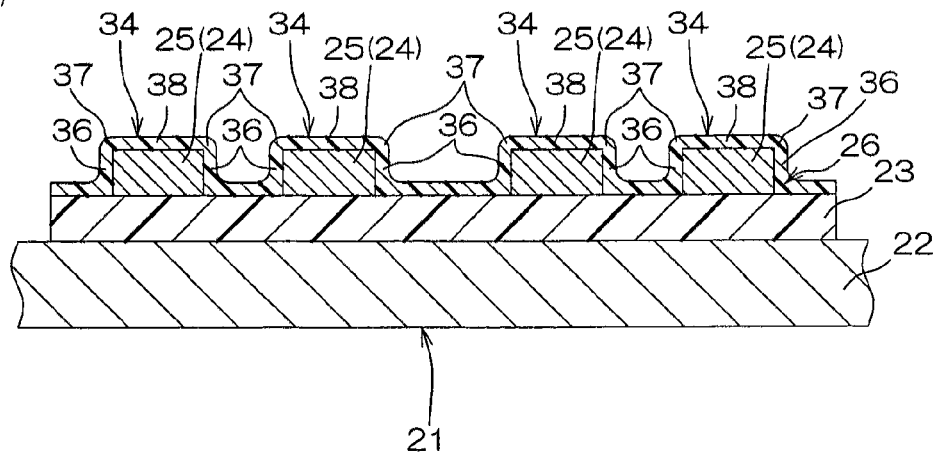

FIG.4
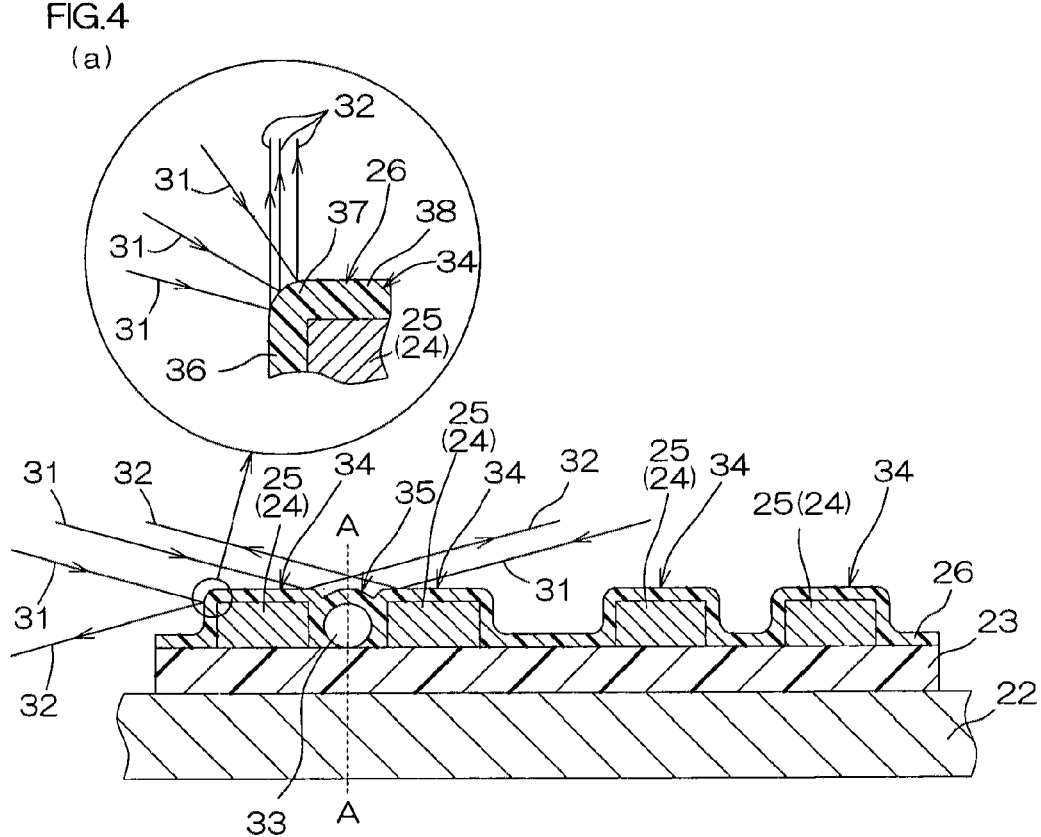
(a)
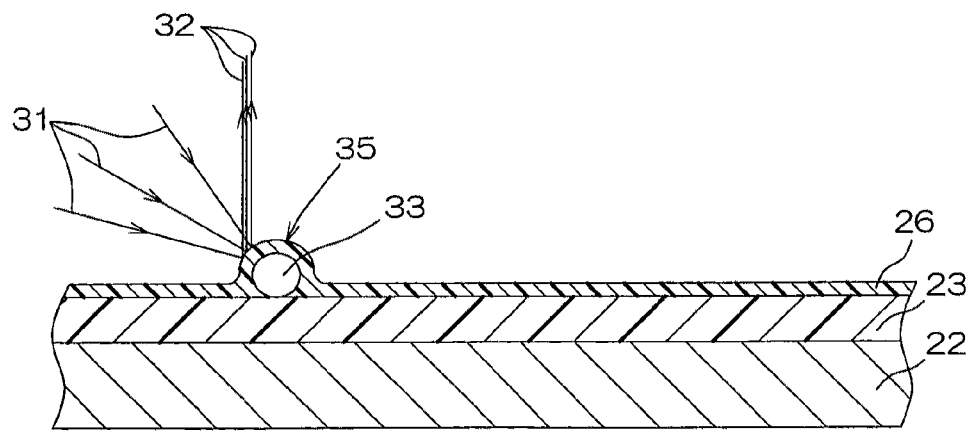
(b)

INSPECTION DEVICE AND PRODUCING METHOD OF WIRED CIRCUIT BOARD

CROSS-REFERENCE TO RELATED APPLICATION

The present application claims priority from Japanese Patent Application No. 2010-207563 filed on Sep. 16, 2010, the contents of which are hereby incorporated by reference into this application.

BACKGROUND OF THE INVENTION

1. Field of the Invention

The present invention relates to an inspection device and a producing method of a wired circuit board, to be specific, to an inspection device for inspecting the presence or absence of a foreign object in an insulating cover layer of the wired circuit board and a producing method of the wired circuit board used by the inspection device.

2. Description of Related Art

Conventionally, a wired circuit board such as a suspension board with circuit has included a metal supporting layer, and an insulating base layer, a conductive pattern and an insulating cover layer that are sequentially laminated thereon. In the wired circuit board, after the formation of the insulating cover layer, the presence or absence of a foreign object in the insulating cover layer has been inspected by using an automatic visual inspection (AVI: Automatic Visual Inspection) device that inspects the entire appearance of the wired circuit board.

There has been proposed, for example, as the AVI device, an inspection device which is provided with an upper illumination means, a horizontal illumination means and a microscope is arranged in opposed relation onto a long film carrier tape provided with an insulating film, a wiring pattern formed thereon and a cover lay layer covering the wiring pattern (ref: for example, Japanese Unexamined Patent Publication No. 2007-42956).

In the inspection device, the upper illumination means is formed as a ring light that uses a LED as a light source and applies light to the film carrier tape so that an incident angle thereof with respect to the vertical direction is in the range of 3 to 45 degrees.

On the lower side of the upper illumination means, the horizontal illumination means extends linearly and is formed from a pair of fluorescent lights that are spaced in opposed relation to each other. The horizontal illumination means applies light to the film carrier tape so that an incident angle thereof with respect to the vertical direction is in the range of 45 to 90 degrees.

The light from the above-described upper illumination means and the horizontal illumination means is reflected on the film carrier tape, and the reflected light is read with a microscope, so that the film carrier tape is inspected.

SUMMARY OF THE INVENTION

In the inspection device described in the above-described Japanese Unexamined Patent Publication No. 2007-42956, the horizontal illumination means applying light that is near horizontal with respect to the film carrier tape is formed from a pair of fluorescent lights in a linear state.

Therefore, when, along the opposing direction of both of the fluorescent lights, a concave portion and a convex portion are continuous alternately and a relatively small convex portion is present between two relatively large convex portions (to be specific, when a plurality of the wiring patterns of the film carrier tape are arranged in parallel and a small foreign object is present between two wiring patterns), there may be a case where the small convex portion is included in the shadow of the two large convex portions, so that it becomes difficult to detect the small convex portion.

That is, there is a disadvantage that the presence or absence of a minute foreign object can not be inspected accurately.

It is an object of the present invention to provide an inspection device that is capable of inspecting the presence or absence of a foreign object in an insulating cover layer accurately and a producing method of a wired circuit board.

An inspection device of the present invention described above, for inspecting the presence or absence of a foreign object in an insulating cover layer in a wired circuit board provided with an insulating base layer, a conductive pattern formed on the insulating base layer and the insulating cover layer formed on the insulating base layer so as to cover the conductive pattern, includes a light emitting unit emitting incident light that enters the insulating cover layer and a light receiving unit receiving reflected light that is reflected from the incident light on the surface of the insulating cover layer, wherein the light emitting unit includes a first light emitting portion in a ring state that emits the incident light so that the angle thereof with respect to the surface of the insulating base layer is in the range of 25° or less and a second light emitting portion in a ring state that emits the incident light so that the angle thereof with respect to the surface of the insulating base layer is in the range of 35 to 65°.

According to the inspection device of the present invention, it is preferable that the light emitting unit further includes a third light emitting portion in a ring state that emits the incident light so that the angle thereof with respect to the surface of the insulating base layer is in the range of 15 to 45°.

According to the inspection device of the present invention, it is preferable that the wavelength of the incident light is in the range of 450 to 750 nm.

According to the inspection device of the present invention, it is preferable that the transmittance of the incident light with respect to the insulating cover layer is in the range of 30% or less.

According to the inspection device of the present invention, it is preferable that the reflectance of the incident light with respect to the insulating cover layer is in the range of 10 to 30%.

The method for producing a wired circuit board of the present invention includes the steps of forming an insulating base layer; forming a conductive pattern on the insulating base layer; forming an insulating cover layer on the insulating base layer so as to cover the conductive pattern; and inspecting the presence or absence of a foreign object in the insulating cover layer by using the above-described inspection device.

According to the inspection device of the present invention, the light emitting unit emitting incident light that enters the insulating cover layer is provided with the first light emitting portion in a ring state that emits the incident light so that the angle thereof with respect to the surface of the insulating base layer is in the range of 25° or less and the second light emitting portion in a ring state that emits the incident light so that the angle thereof with respect to the surface of the insulating base layer is in the range of 35 to 65°.

Therefore, both of the incident light that enters the insulating cover layer from the first light emitting portion at a shallow angle (the angle with respect to the surface of the insulating base layer is in the range of 25° or less) and the incident light that enters the insulating cover layer from the second light emitting portion at a deep angle (the angle with respect to the surface of the insulating base layer is in the range of 35 to 65°) enter circularly.

In this way, it is possible that the incident light that enters at a shallow angle and the incident light that enters at a deep angle enter a minute convex portion of the insulating cover layer from all of the directions, so that the minute convex portion can be detected accurately.

As a result, the presence or absence of a foreign object in the insulating cover layer can be detected accurately.

According to the method for producing the wired circuit board that uses the inspection device, the foreign object that is present in the insulating cover layer can be detected accurately, so that a fine pitch of the wired circuit board can be achieved.

BRIEF DESCRIPTION OF THE DRAWINGS

FIG. 3 shows process drawings for describing a method for producing a wired circuit board of the present invention:
(a) illustrating a step of preparing a metal supporting board,
(b) illustrating a step of forming an insulating base layer,
(c) illustrating a step of forming a conductive pattern, and
(d) illustrating a step of forming an insulating cover layer.

FIG. 4 shows explanation drawings for describing a process of inspecting the presence or absence of a foreign object in the insulating cover layer:
(a) illustrating a sectional view showing a state where the foreign object is present between two wires and
(b) illustrating an A-A sectional view of (a).

DETAILED DESCRIPTION OF THE INVENTION

Figure 1:
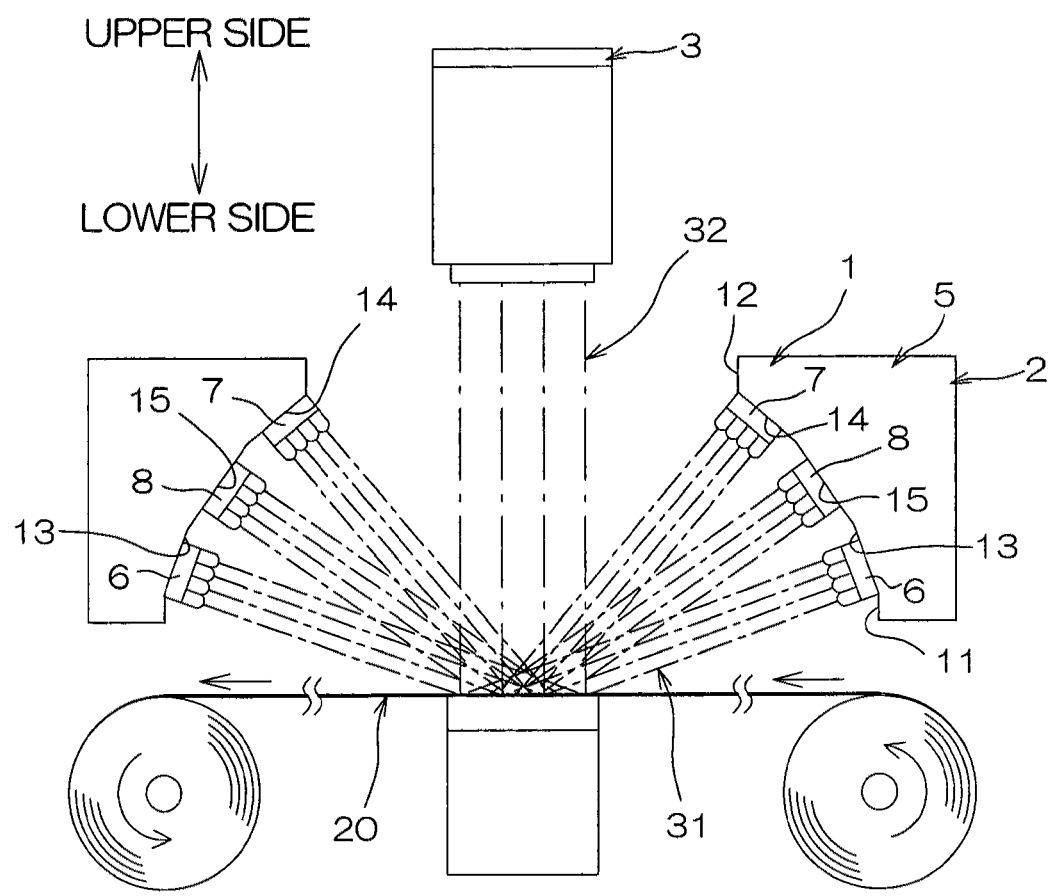
FIG. 1 shows a schematic configuration view of one embodiment of an inspection device of the present invention.
Figure 2:
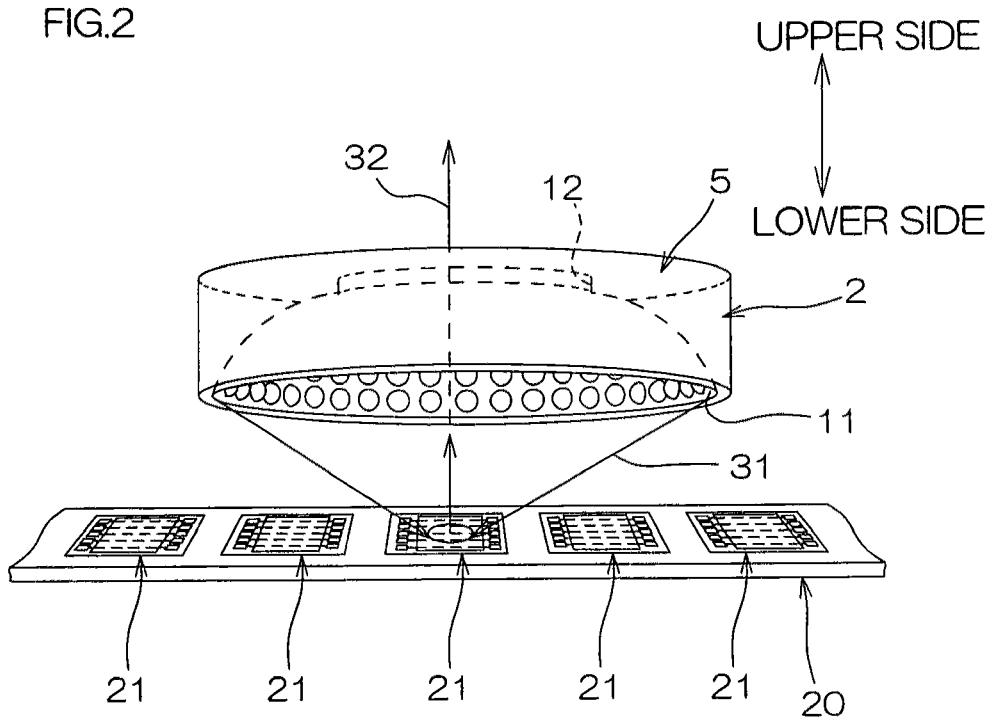
FIG. 2 shows a perspective view of the inspection device shown in FIG. 1.

FIG. 1 shows a schematic configuration view of one embodiment of an inspection device of the present invention. FIG. 2 shows a perspective view of the inspection device shown in FIG. 1.

As shown in FIGS. 1 and 2, an inspection device 1 is an AVI device for inspecting the presence or absence of a foreign object in an insulating cover layer 26 (described later) of a suspension board with circuit 21 (described later) and a detecting method of a so-called ring illumination is used thereto.

The inspection device 1 includes a light source unit 2 as a light emitting unit and a camera unit 3 as a light receiving unit.

The light source unit 2 is a so-called ring illumination and emits incident light 31 that enters the insulating cover layer 26. The light source unit 2 includes a frame 5, a first light emitting portion 6, a second light emitting portion 7, and a third light emitting portion 8.

The frame 5 is formed into a generally cylindrical shape having a dome-shaped inner surface. To be specific, in the frame 5, an incident side opening 11 for allowing the incident light 31 that enters the suspension board with circuit 21 (described later) to pass through and a reflection side opening 12 for allowing reflected light 32 from the suspension board with circuit 21 (described later) to pass through are formed.

The incident side opening 11 is formed into a generally circular shape that shares the center with the frame 5 at one end portion in the axial direction of the frame 5.

The reflection side opening 12 is formed into a generally circular shape whose diameter is smaller than that of the incident side opening 11 so as to share the center with the frame 5 at the other end portion in the axial direction of the frame 5.

The inner surface of the frame 5 is, from the incident side opening 11 toward the reflection side opening 12, gradually reduced in diameter with being continuously curved and is formed into a dome shape.

To be specific, in the inner surface of the frame 5, a first surface 13 that is continuous to the incident side opening 11, a second surface 14 that is continuous to the reflection side opening 12, and a third surface 15 that is continuous to a spacing between the first surface 13 and the second surface 14 are formed.

The first surface 13 is inclined so as to form an angle of about 10° with respect to the central axis of the frame 5 and is formed along the circumferential direction of the frame 5.

The second surface 14 is inclined so as to form an angle of about 50° with respect to the central axis of the frame 5 and is formed along the circumferential direction of the frame 5.

The third surface 15 is inclined so as to form an angle of about 30° with respect to the central axis of the frame 5 and is formed along the circumferential direction of the frame 5.

That is, the inner surface of the frame 5 is, from the incident side opening 11 toward the reflection side opening 12, gradually reduced in diameter with being curved so that the first surface 13, the third surface 15, and the second surface 14 are sequentially continuous and is formed into a dome shape.

The first light emitting portion 6 is formed into a generally circular ring shape that shares the central axis with the frame 5 and is provided on the first surface 13 of the frame 5. The first light emitting portion 6 includes, as a light source, for example, a LED (light emitting diode), fluorescent light, incandescent light, halogen light, and the like. Preferably, the first light emitting portion 6 includes a LED from the viewpoint of the wavelength of the incident light 31. More preferably, the first light emitting portion 6 includes a plurality of the LEDs that are arranged in alignment.

The first light emitting portion 6 emits the incident light 31 so as to form an angle of $10\pm\alpha°$ with respect to a plane that is perpendicular to the central axis of the frame 5. To be specific, the first light emitting portion 6 emits the incident light 31 so as to form an angle in the range of 25° or less, or preferably 20° or less, or more preferably 15° or less with respect to a plane that is perpendicular to the central axis of the frame 5.

The second light emitting portion 7 is formed into a generally circular ring shape that shares the central axis with the frame 5 and is provided on the second surface 14 of the frame 5. The second light emitting portion 7 is provided with the same light source as that of the first light emitting portion 6.

The second light emitting portion 7 emits the incident light 31 so as to form an angle of $50\pm\alpha°$ with respect to a plane that is perpendicular to the central axis of the frame 5. To be specific, the second light emitting portion 7 emits the incident light 31 so as to form an angle in the range of 35 to 65°, or preferably 40 to 60°, or more preferably 45 to 55° with respect to a plane that is perpendicular to the central axis of the frame 5.

The third light emitting portion 8 is formed into a generally circular ring shape that shares the central axis with the frame 5 and is provided on the third surface 15 of the frame 5. The third light emitting portion 8 is provided with the same light source as that of the first light emitting portion 6.

The third light emitting portion 8 emits the incident light 31 so as to form an angle of $30\pm\alpha°$ with respect to a plane that is perpendicular to the central axis of the frame 5. To be specific, the third light emitting portion 8 emits the incident light 31 so as to form an angle in the range of 15 to 45°, or preferably 20 to 40°, or more preferably 25 to 35° with respect to a plane that is perpendicular to the central axis of the frame 5.

In the following description, the median of the angle (10° in the first light emitting portion 6, 50° in the second light emitting portion 7, 30° in the third light emitting portion 8) formed by a plane that is perpendicular to the central axis of the frame 5 and by each of the incident lights 31 emitted from each of the light emitting portions (the first light emitting portion 6, the second light emitting portion 7, and the third light emitting portion 8) may be described as the optical axis angle of each of the light emitting portions.

The wavelength of the incident light 31 emitted from the first light emitting portion 6, the second light emitting portion 7 and the third light emitting portion 8 is in the range of, for example, 450 to 750 nm, or preferably 550 to 750 nm.

When the wavelength of the incident light 31 is within the above-described range, a light source that has a large amount of light emitted can be selected as a light source of the light source unit 2 and a camera that has a large amount of light received (highly sensitive) can be selected as a camera of the camera unit 3. In this way, the insulating cover layer 26 is illuminated by the bright light source unit 2 and the reflected light 32 from the insulating cover layer 26 can be efficiently received by the highly sensitive camera unit 3, so that a concave portion and a convex portion of the insulating cover layer 26 can be detected accurately even when the reflectance of the insulating cover layer 26 is low.

The light source unit 2 is provided spaced apart above a suspension board with circuit assembly sheet 20 (described later) so that the central axis of the frame 5 is along the thickness direction (described later) of the suspension board with circuit 21 (described later).

The camera unit 3 is disposed on the other side of the frame 5 in the axial direction so as to be disposed in opposed relation to the reflection side opening 12 of the light source unit 2. The camera unit 3 is provided with a camera such as a near-infrared camera, a CCD camera, and the like. Preferably, the camera unit 3 is provided with a CCD camera from the viewpoint of versatility.

The inspection device 1 is configured such that the suspension board with circuit assembly sheet 20 (described later) is conveyable so that the incident light 31 is applied to the suspension board with circuit 21 (described later) that is the test object.

FIG. 3 shows process drawings for describing a method for producing a wired circuit board of the present invention. FIG. 4 shows explanation drawings for describing a process of inspecting the presence or absence of a foreign object in the insulating cover layer: (a) illustrating a sectional view showing a state where the foreign object is present between two wires and (b) illustrating an A-A sectional view of (a). In FIG. 3, the right-left direction of the paper surface is referred to as the widthwise direction of the suspension board with circuit 21, the up-down direction of the paper surface being referred to as the thickness direction of the suspension board with circuit 21, and the thickness direction of the paper being referred to as the lengthwise direction of the suspension board with circuit 21.

Next, a method for producing the suspension board with circuit 21 as a wired circuit board of the present invention is described with reference to FIG. 3. In FIG. 3, one suspension board with circuit 21 is shown. However, in the embodiment, a plurality of the suspension boards with circuits 21 are produced at the same time without being produced individually.

To be specific, the suspension board with circuit assembly sheet 20 integrally having a plurality of the suspension boards with circuits 21 is produced by patterning a plurality of the suspension boards with circuits 21 on a long metal supporting layer 22 (described later) so that a plurality of the suspension boards with circuits 21 are arranged in parallel at spaced intervals to each other. When the suspension boards with circuits 21 are mounted on a hard disk drive, for example, the suspension boards with circuits 21 are individually taken out from the suspension board with circuit assembly sheet 20 to be mounted thereon.

To produce the suspension board with circuit 21, as shown in FIG. 3 (a), the metal supporting layer 22 in a sheet shape is first prepared.

An example of the material for forming the metal supporting layer 22 includes a metal material such as stainless steel, 42-alloy, aluminum, copper-beryllium, or phosphor bronze. Preferably, stainless steel is used.

The metal supporting layer 22 has a thickness in the range of, for example, 10 to 50 μm, or preferably 15 to 35 μm.

Next, to produce the suspension board with circuit 21, as shown in FIG. 3 (b), in the portion where a conductive pattern 24 is formed, an insulating base layer 23 is formed on the metal supporting layer 22.

An example of the material for forming the insulating base layer 23 includes a synthetic resin such as polyimide, polyamide imide, acrylic, polyether nitrile, polyether sulfone, polyethylene terephthalate (PET), polyethylene naphthalate, and polyvinyl chloride. Preferably, polyimide is used from the viewpoint of thermal dimensional stability and the like.

In addition, for example, the insulating base layer 23 is formed from a synthetic resin obtained by curing an uncured resin.

That is, for example, a solution of an uncured resin having photosensitivity such as a photosensitive polyamic acid resin is first applied onto the metal supporting layer 22 and is then dried, so that a photosensitive layer is formed. Next, the photosensitive layer is exposed to light via a photo mask and is then developed to be dried, so that an uncured resin layer (not shown) made of an uncured resin is formed with the above-described pattern.

Thereafter, the uncured resin layer is cured, so that the insulating base layer 23 made of a synthetic resin is formed. Examples of a curing method for the uncured resin layer include photocuring by electron beam, ultraviolet rays, and the like and heat curing. Preferably, heat curing is used. The heating temperature in the heat curing is in the range of, for example, 300 to 500° C., or preferably 360 to 440° C.

Furthermore, the insulating base layer 23 can also be formed, for example, by preliminarily forming a synthetic resin into a film having the above-described pattern and adhesively bonding the film to the surface of the metal supporting layer 22 via a known adhesive layer.

The insulating base layer 23 has a thickness in the range of, for example, 3 to 20 μm, or preferably 3 to 10 μm.

Next, to produce the suspension board with circuit 21, as shown in FIG. 3 (c), the conductive pattern 24 is formed on the insulating base layer 23 with a predetermined pattern.

To be specific, the conductive pattern 24 is formed with a pattern where the conductive pattern 24 includes a plurality (four pieces) of wires 25 that are arranged in parallel at spaced intervals to each other along the widthwise direction, each of head-side terminals (not shown) that is provided at one end portion of each of the wires 25 in the lengthwise direction, and each of external terminals (not shown) that is provided at the other end portion of each of the wires 25 in the lengthwise direction.

An example of the material for forming the conductive pattern 24 includes a conductive material such as copper, nickel, gold, solder, or alloys thereof. Preferably, copper is used.

To form the conductive pattern 24, a known patterning method such as an additive method or a subtractive method is used. Preferably, the additive method is used.

In the additive method, to be specific, a conductive seed film is first formed on the surface of the metal supporting layer 22 including the insulating base layer 23 by a sputtering method and the like. Next, a plating resist is formed on the surface of the conductive seed film in a pattern reverse to that of the conductive pattern 24. Thereafter, the conductive pattern 24 is formed on the surface of the conductive seed film on the insulating base layer 23 exposed from the plating resist by electrolytic plating. Subsequently, the plating resist and the conductive seed film on the portion where the plating resist is laminated are removed.

The conductive pattern 24 has a thickness in the range of, for example, 3 to 30 μm, or preferably 5 to 20 μm. When the thickness of the conductive pattern 24 is below the above-described range, there may be a case where a raise of a wire side raised portion 34 (described later) is insufficient.

The width of each of the wires 25 may be the same or different from each other and is in the range of, for example, 5 to 500 μm, or preferably 10 to 200 μm. The spacing between each of the wires 25 may be the same or different from each other and is in the range of, for example, 5 to 200 μm, or preferably 5 to 100 μm.

Next, to produce the suspension board with circuit 21, as shown in FIG. 3 (d), the insulating cover layer 26 is formed on the insulating base layer 23 so as to cover each of the wires 25 and to expose each of the head-side terminals (not shown) and each of the external terminals (not shown).

A material for forming the insulating cover layer 26 includes the same material as that for forming the above-described insulating base layer 23. Preferably, polyimide is used.

In addition, the insulating cover layer 26 is, in the portion corresponding to the wires 25, formed so as to cover the upper surfaces of the wire 25 and the both side surfaces thereof in the widthwise direction. In this way, the wire side raised portion 34 that is raised corresponding to the sectional shape of the wire 25 is formed on the insulating cover layer 26. Moreover, among the insulating cover layer 26, the portion corresponding to the spacing between each of the wires 25 is formed so as to dent with respect to the wire side raised portion 34.

Furthermore, the wire side raised portion 34 includes a first flat portion 36 that covers the both end surfaces of the wire 25 in the widthwise direction, a shoulder portion 37 that is continuous to the first flat portion 36 and curves upward so as to cover the upper corner portions of the both end portions of the wire 25 in the widthwise direction, and a second flat portion 38 that is continuous to the shoulder portion 37 to cover the upper surface of the wire 25.

The transmittance T of the incident light 31 with respect to the insulating cover layer 26 (the transmittance with respect to the insulating cover layer 26 having a thickness of 17 μm) is in the range of, for example, 30% or less, or preferably 15% or less and usually 0% or more. The transmittance T is measured with a spectral photometer.

When the transmittance T of the incident light 31 with respect to the insulating cover layer 26 is within the above-described range, it is possible to suppress that the incident light 31 transmits through the insulating cover layer 26. In this way, the influence (such as a case where the incident light 31 is reflected on the surface of the conductive pattern 24 to be received in the camera unit 3) of the incident light 31 that transmits through the insulating cover layer 26 can be reduced and the reflected light 32 that is reflected on the surface of the insulating cover layer 26 can be efficiently received in the camera unit 3.

The reflectance (the incident angle of 0 degree) R of the incident light 31 with respect to the insulating cover layer 26 is in the range of, for example, 10 to 30%, or preferably 10 to 15%.

The thickness of the insulating cover layer 26 (that is, in the portion where the wire 25 is covered, the length from the surface (the upper surface and the side surfaces) of the wire 25 to the surface (the upper surface and the side surfaces) of the insulating cover layer 26, and in the portion where the insulating base layer 23 that is exposed from the wire 25 is covered, the length from the surface (the upper surface) of the insulating base layer 23 to the surface (the upper surface) of the insulating cover layer 26) is in the range of, for example, 50 μm or less, or preferably 20 μm or less and usually 1 μm or more, or preferably 3 μm or more. When the thickness of the insulating cover layer 26 is above the above-described range, it may be difficult to detect the wire side raised portion 34 accurately.

Next, to produce the suspension board with circuit 21, the presence or absence of a foreign object in the insulating cover layer 26 is inspected by using the above-described inspection device 1.

The inspection of the insulating cover layer 26 is performed, as shown in FIG. 1, with the inspection device 1, by conveying the suspension board with circuit assembly sheet 20 so that the incident light 31 is applied to the suspension board with circuit 21.

The incident light 31 emitted from the first light emitting portion 6 enters the insulating cover layer 26 so that the angle thereof with respect to the surface of the insulating base layer 23 is $10\pm\alpha°$. To be specific, the incident light 31 emitted from the first light emitting portion 6 enters the insulating cover layer 26 so that the angle thereof with respect to the surface of the insulating base layer 23 is in the range of 25° or less, or preferably 20° or less, or more preferably 15° or less.

The incident light 31 emitted from the second light emitting portion 7 enters the insulating cover layer 26 so that the angle thereof with respect to the surface of the insulating base layer 23 is 50±α°. To be specific, the incident light 31 emitted from the second light emitting portion 7 enters the insulating cover layer 26 so that the angle thereof with respect to the surface of the insulating base layer 23 is in the range of 35 to 65°, or preferably 40 to 60°, or more preferably 35 to 55°.

The incident light 31 emitted from the third light emitting portion 8 enters the insulating cover layer 26 so that the angle thereof with respect to the surface of the insulating base layer 23 is 30±α°. To be specific, the incident light 31 emitted from the third light emitting portion 8 enters the insulating cover layer 26 so that the angle thereof with respect to the surface of the insulating base layer 23 is in the range of 15 to 45°, or preferably 20 to 40°, or more preferably 25 to 35°.

The incident light 31 is reflected on the surface of the insulating cover layer 26. Among the reflected light 32, the reflected light 32 that is reflected on the shoulder portion 37 of the wire side raised portion 34 is mainly detected with the camera unit 3.

To be specific, among the incident light 31 from the first light emitting portion 6, as shown in an enlarged state in FIG. 4 (a), the incident light 31 that enters the neighborhood of the lower end portion of the shoulder portion 37 is reflected upward toward the camera unit 3, so that the reflected light 32 is detected with the camera unit 3.

In addition, among the incident light 31 from the second light emitting portion 7, the incident light 31 that enters the neighborhood of the upper end portion of the shoulder portion 37 is reflected upward toward the camera unit 3, so that the reflected light 32 is detected with the camera unit 3.

Furthermore, among the incident light 31 from the third light emitting portion 8, the incident light 31 that enters the neighborhood of the center of the shoulder portion 37 in the up-down direction is reflected upward toward the camera unit 3, so that the reflected light 32 is detected with the camera unit 3.

On the other hand, among the incident light 31, the incident light 31 that enters the flat portion of the insulating cover layer 26 (the portion other than the shoulder portion 37) is reflected in the opposite direction to the incident direction thereof without being reflected toward the camera unit 3, so that the reflected light 32 is not detected with the camera unit 3.

In this way, when the insulating cover layer 26 of the suspension board with circuit 21 is photographed with the camera unit 3, the portion other than the shoulder portion 37 is photographed darkly while the shoulder portion 37 of the wire side raised portion 34 is photographed brightly.

When a foreign object 33 such as a metal powder, a resin powder, and air is mixed in the insulating cover layer 26, the insulating cover layer 26 is also raised in the portion where the foreign object 33 is mixed, so that a foreign object side raised portion 35 corresponding to the foreign object 33 is formed.

Then, the incident light 31 is, in the foreign object side raised portion 35, also reflected upward toward the camera unit 3 in the same manner as in the above-described wire side raised portion 34, so that the reflected light 32 is detected with the camera unit 3.

In this way, the foreign object side raised portion 35 is photographed brightly with the camera unit 3, so that the foreign object 33 can be detected.

To be specific, when the foreign object 33 having a shorter length in the thickness direction than the thickness of the wire 25 is present between the two wires 25, as shown in FIG. 4 (b), the foreign object 33 can be detected by the incident light 31 that enters the foreign object side raised portion 35 from the direction that the wires 25 extend (in this embodiment, the same direction as the lengthwise direction of the suspension board with circuit 21).

The suspension board with circuit 21 in which the foreign object 33 is detected is judged to be a defective product to be removed and the suspension board with circuit 21 in which the foreign object 33 is not detected is judged to be a non-defective product to be made a product.

The suspension board with circuit 21 is obtained in this manner.

According to the inspection device 1, as shown in FIGS. 1 and 4, the light source unit 2 emitting the incident light 31 that enters the insulating cover layer 26 is provided with the first light emitting portion 6 in a ring state that emits the incident light 31 so that the angle thereof with respect to the surface of the insulating base layer 23 is in the range of 25° or less and the second light emitting portion 7 in a ring state that emits the incident light 31 so that the angle thereof with respect to the surface of the insulating base layer 23 is in the range of 35 to 65°.

Therefore, both of the incident light 31 that enters the insulating cover layer 26 from the first light emitting portion 6 at a shallow angle (the angle with respect to the surface of the insulating base layer 23 is in the range of 25° or less) and the incident light 31 that enters the insulating cover layer 26 from the second light emitting portion 7 at a deep angle (the angle with respect to the surface of the insulating base layer 23 is in the range of 35 to 65°) enter circularly.

In this way, it is possible that the incident light 31 that enters at a shallow angle and the incident light 31 that enters at a deep angle enter the minute foreign object side raised portion 35 of the insulating cover layer 26 from all of the directions, so that the minute foreign object side raised portion 35 can be detected accurately.

As a result, the presence or absence of the foreign object 33 in the insulating cover layer 26 can be detected accurately.

In addition, according to the inspection device 1, as shown in FIGS. 1 and 4, the light source unit 2 is further provided with the third light emitting portion 8 in a ring state that emits the incident light 31 so that the angle thereof with respect to the surface of the insulating base layer 23 is in the range of 15 to 45°.

Therefore, the minute foreign object side raised portion 35 can be detected more accurately, so that the presence or absence of the foreign object 33 in the insulating cover layer 26 can be detected more accurately.

According to the method for producing the suspension board with circuit 21 that uses the inspection device 1, the foreign object 33 that is present in the insulating cover layer 26 can be detected accurately, so that a fine pitch of the suspension board with circuit 21 can be achieved.

EXAMPLE

While the present invention will be described hereinafter in further detail with reference to Examples and Comparative Examples, the present invention is not limited to these Examples and Comparative Examples.

Example 1

First, a metal supporting layer made of stainless steel having a thickness of 18 μm was prepared (ref: FIG. 3 (a)). Next, a varnish of a photosensitive polyamic acid resin was applied to the surface of the metal supporting layer and was then dried. Thereafter, the dried varnish was exposed to light and was then developed to be heat cured, so that an insulating base layer made of polyimide having a thickness of 10 µm was formed into the above-described pattern (ref: FIG. 3 (b)).

Next, as a conductive thin film, a chromium thin film having a thickness of 0.03 µm and a copper thin film having a thickness of 0.07 µm were successively formed on the surface of the insulating base layer including the metal supporting layer by chromium sputtering and copper sputtering. Subsequently, a plating resist in a pattern reverse to that of the conductive pattern was formed on the surface of the conductive thin film. Then, the conductive pattern having a thickness of 12 µm was formed on the surface of the conductive thin film exposed from the plating resist by electrolytic copper plating. Thereafter, the plating resist and the conductive thin film on the portion where the plating resist was formed were removed by chemical etching (ref: FIG. 3 (c)).

Next, a varnish of a photosensitive polyamic acid resin was applied to the surface of the insulating base layer including the conductive pattern and was then dried. Thereafter, the dried varnish was exposed to light and was then developed to be heat cured, so that an insulating cover layer made of polyimide having a thickness of 17 µm was formed with a pattern of covering the wires and exposing the head-side terminals and the external terminals (ref: FIG. 3 (d)). On the insulating cover layer, a wire side raised portion was formed by raising the portion that covered the wires.

The transmittance T of the light in the wavelength of 620 nm with respect to the insulating cover layer was 12% and the reflectance R (the incident angle of 0°) of the light in the wavelength of 620 nm with respect to the insulating cover layer was 10%. The transmittance T and the reflectance R were measured with a spectral photometer (V-670; ultraviolet, visible, and near-infrared spectral photometer; manufactured by JASCO Corporation.).

When the insulating cover layer was formed, air was mixed in the insulating cover layer between the two wires, so that voids with three different sizes of large, medium, and small were formed. On the insulating cover layer, a foreign object side raised portion was formed by raising the portions where each of the voids was formed.

The size of the void (large) that was formed was as follows: the length in the thickness direction of 20 µm, the length in the widthwise direction of 15 µm, and the length in the lengthwise direction of 100 µm.

The size of the void (medium) that was formed was as follows: the length in the thickness direction of 10 µm, the length in the widthwise direction of 10 µm, and the length in the lengthwise direction of 20 µm.

The size of the void (small) that was formed was as follows: the length in the thickness direction of 5 µm, the length in the widthwise direction of 5 µm, and the length in the lengthwise direction of 10 µm.

Figure 5:
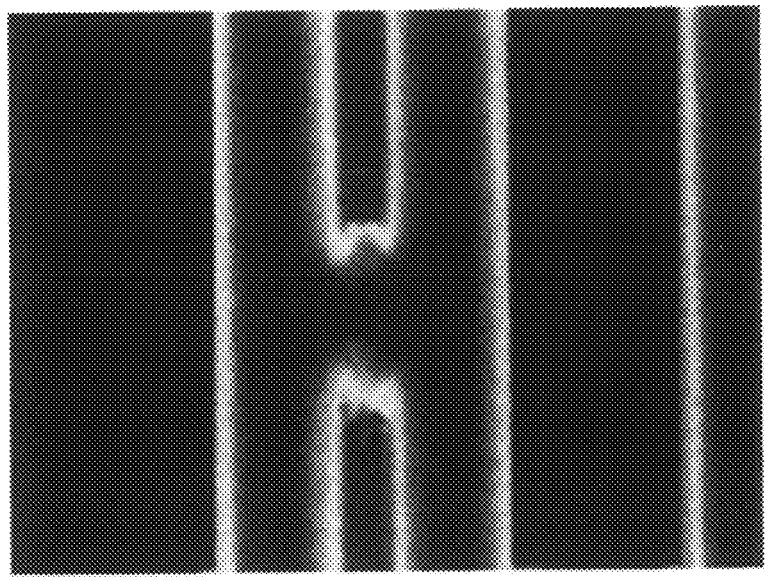
FIG. 5 shows an inspection image of the insulating cover layer in Example 1 and an image of a void (large).
Figure 6:
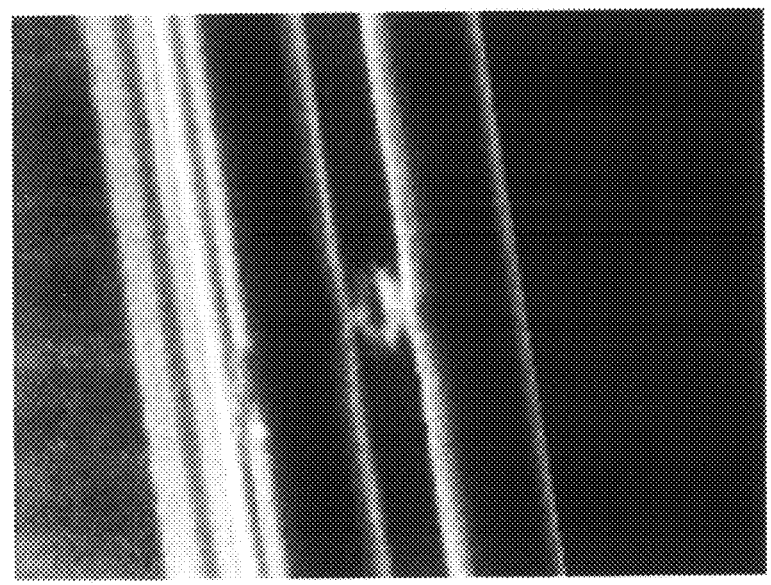
FIG. 6 shows an inspection image of the insulating cover layer in Example 1 and an image of a void (medium).
Figure 7:
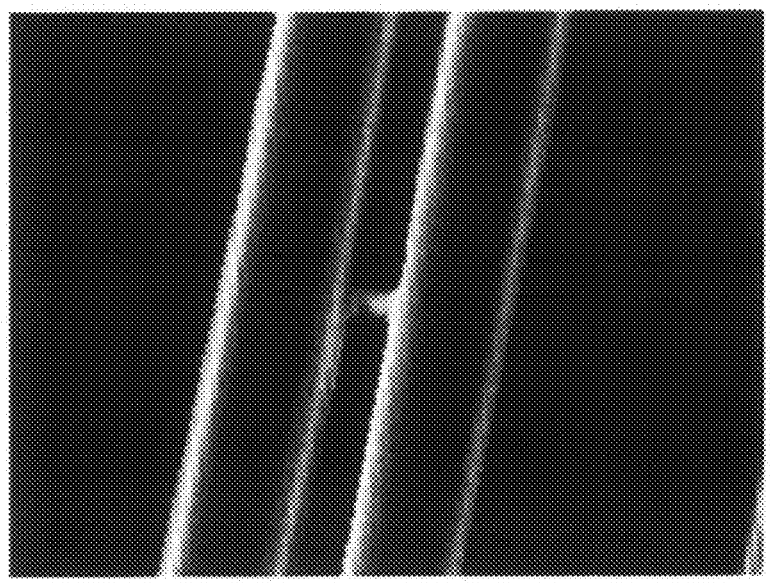
FIG. 7 shows an inspection image of the insulating cover layer in Example 1 and an image of a void (small).

Next, by using the above-described inspection device, the incident light having the wavelength of 620 nm was applied to the insulating cover layer from a first light emitting portion and a second light emitting portion of a light source unit. Then, the reflected light was received with a CCD camera, thereby obtaining an inspection image. The presence or absence of a defect of the insulating cover layer was inspected by analyzing the obtained inspection image. The image of the void (large) is shown in FIG. 5, the image of the void (medium) being shown in FIG. 6, and the image of the void (small) being shown in FIG. 7. The evaluation of the inspection image is shown in the following Table 1.

A suspension board with circuit was obtained in this manner.

Example 2

Figure 8:
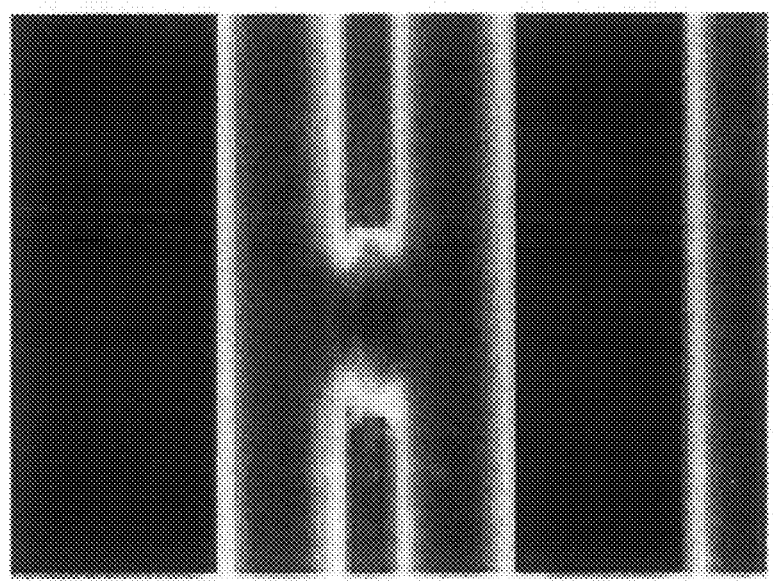
FIG. 8 shows an inspection image of the insulating cover layer in Example 2 and an image of a void (large).
Figure 9:
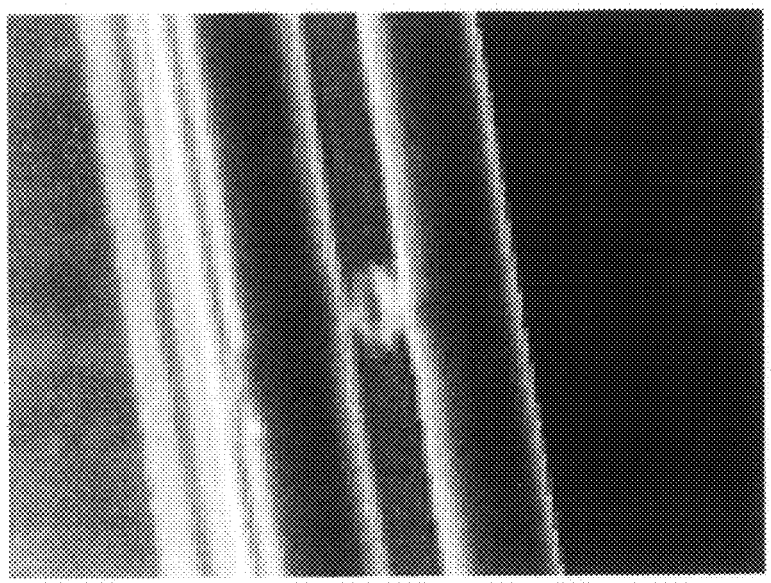
FIG. 9 shows an inspection image of the insulating cover layer in Example 2 and an image of a void (medium).
Figure 10:
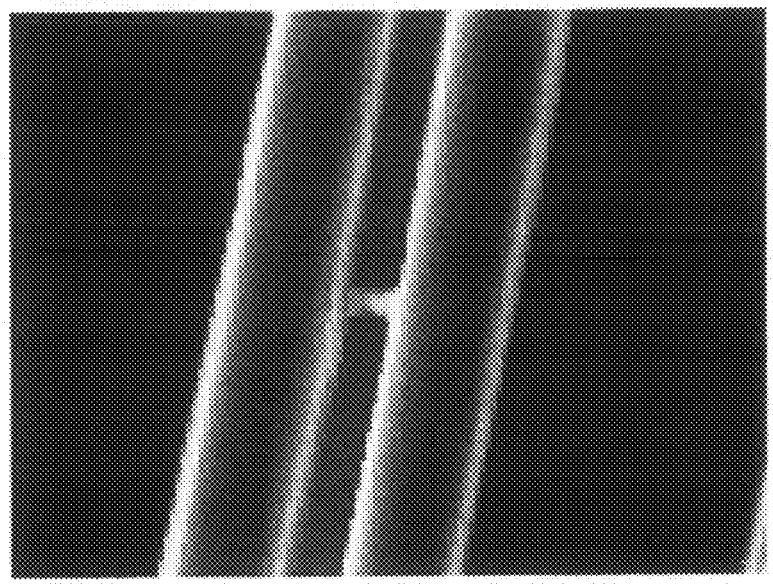
FIG. 10 shows an inspection image of the insulating cover layer in Example 2 and an image of a void (small).

The presence or absence of a defect of an insulating cover layer was inspected in the same manner as in Example 1 except that the incident light having the wavelength of 620 nm was applied to the insulating cover layer from the first light emitting portion, the second light emitting portion, and a third light emitting portion of the light source unit and then, the reflected light was received with the CCD camera, thereby obtaining an inspection image. The image of the void (large) is shown in FIG. 8, the image of the void (medium) being shown in FIG. 9, and the image of the void (small) being shown in FIG. 10. The evaluation of the inspection image is shown in the following Table 1.

Comparative Example 1

Figure 11:
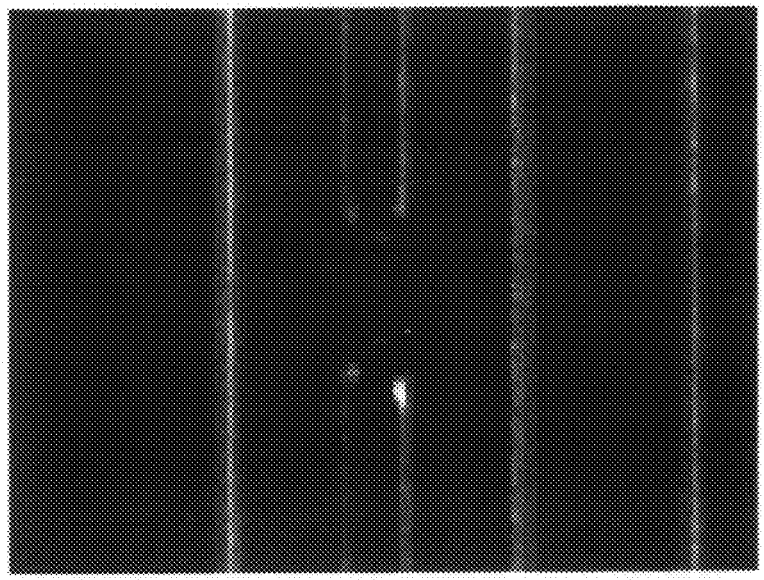
FIG. 11 shows an inspection image of the insulating cover layer in Comparative Example 1 and an image of a void (large).
Figure 12:
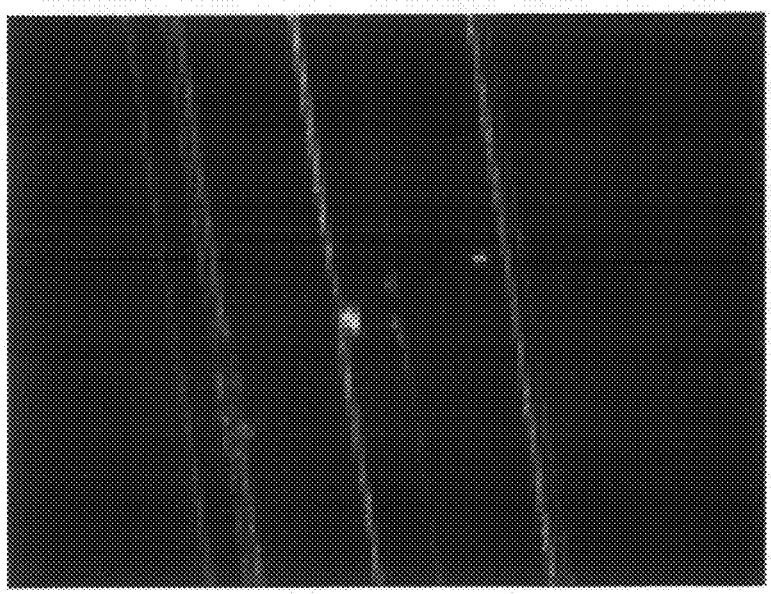
FIG. 12 shows an inspection image of the insulating cover layer in Comparative Example 1 and an image of a void (medium).
Figure 13:
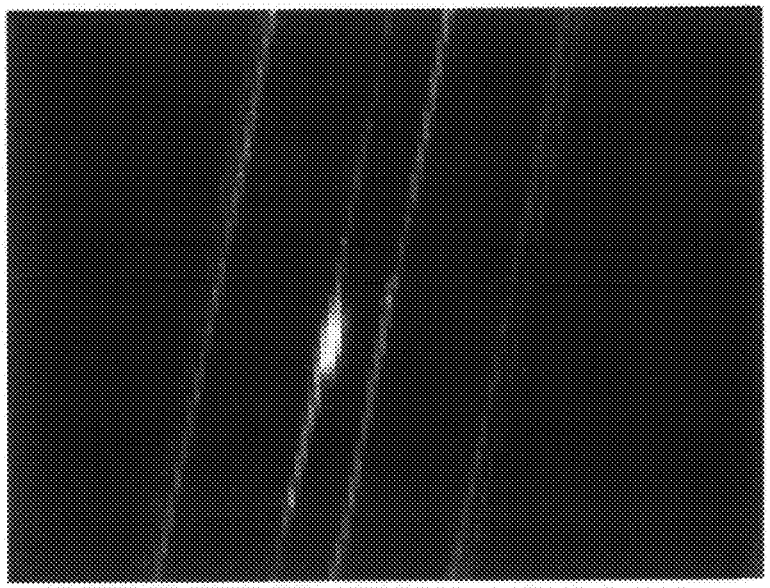
FIG. 13 shows an inspection image of the insulating cover layer in Comparative Example 1 and an image of a void (small).

The presence or absence of a defect of an insulating cover layer was inspected in the same manner as in Example 1 except that a light source having an optical axis angle of 20° was prepared and the incident light having the wavelength of 620 nm was applied to the insulating cover layer from the light source and then, the reflected light was received with the CCD camera, thereby obtaining an inspection image. The image of the void (large) is shown in FIG. 11, the image of the void (medium) being shown in FIG. 12, and the image of the void (small) being shown in FIG. 13. The evaluation of the inspection image is shown in the following Table 1.

Comparative Example 2

Figure 14:
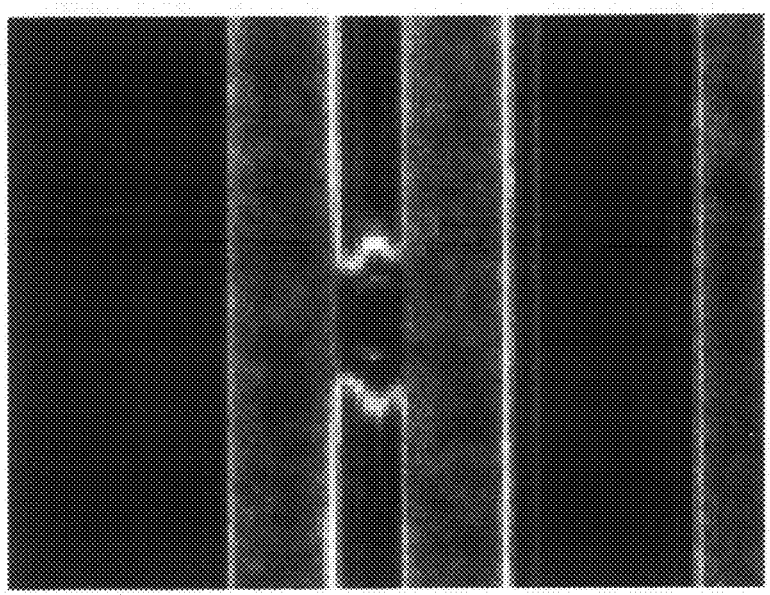
FIG. 14 shows an inspection image of the insulating cover layer in Comparative Example 2 and an image of a void (large).
Figure 15:
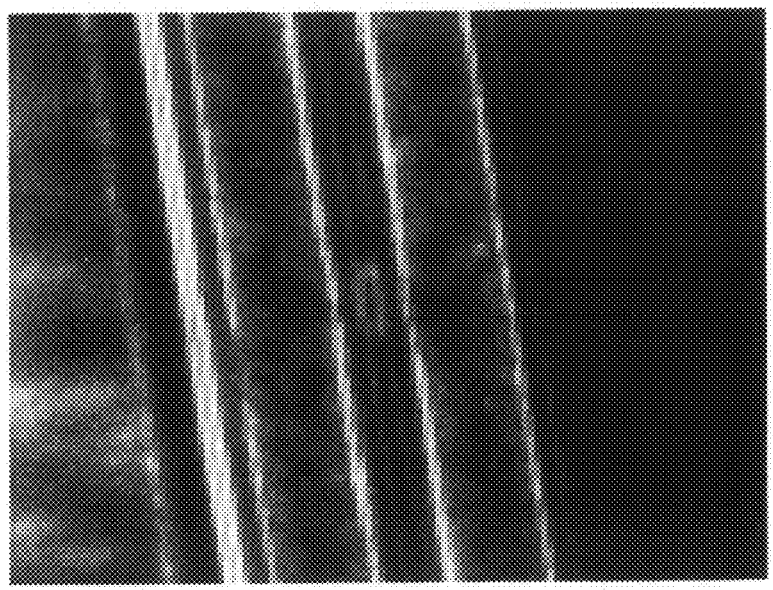
FIG. 15 shows an inspection image of the insulating cover layer in Comparative Example 2 and an image of a void (medium).
Figure 16:
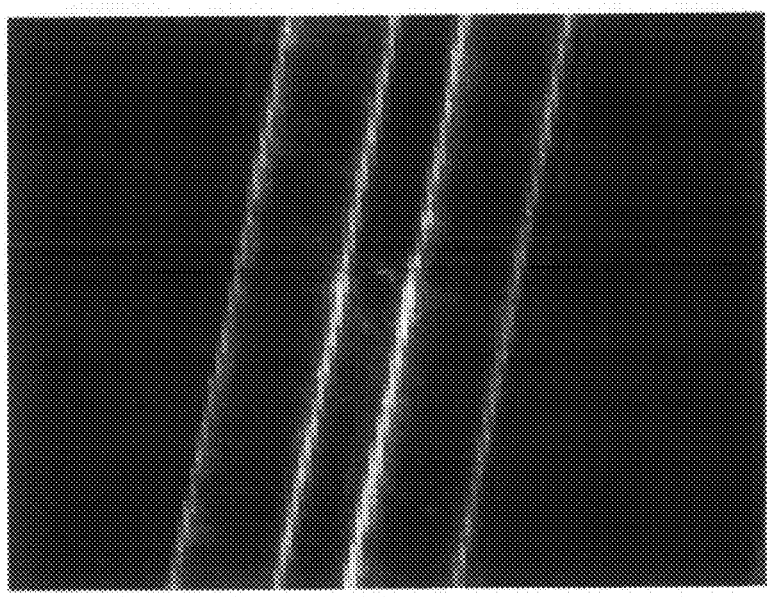
FIG. 16 shows an inspection image of the insulating cover layer in Comparative Example 2 and an image of a void (small).

The presence or absence of a defect of an insulating cover layer was inspected in the same manner as in Example 1 except that a light source having an optical axis angle of 60° was prepared and the incident light having the wavelength of 620 nm was applied to the insulating cover layer from the light source and then, the reflected light was received with the CCD camera, thereby obtaining an inspection image. The image of the void (large) is shown in FIG. 14, the image of the void (medium) being shown in FIG. 15, and the image of the void (small) being shown in FIG. 16. The evaluation of the inspection image is shown in the following Table 1.

TABLE 1

|  |  | Example 1 | Example 2 | Comparative Example 1 | Comparative Example 2 |
|---|---|---|---|---|---|
| Optical Axis Angle |  | 10°, 50° | 10°, 30°, 50° | 20° | 60° |
| Observation of Void | Large | Good | Good | Good | Good |
|  | Medium | Good | Good | Bad | Good |
|  | Small | Good | Good | Bad | Bad |

<Evaluation Criteria of Image Quality>

The inspection images obtained in each of Examples and each of Comparative Examples were observed to evaluate whether the void in the insulating cover layer was photographed sharply or not.

Good: The void in the insulating cover layer was recognized sharply.

Bad: The void in the insulating cover layer was difficult to be recognized.

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

What is claimed is:

1. An inspection device,
for inspecting the presence or absence of a foreign object in an insulating cover layer in a wired circuit board provided with an insulating base layer, a conductive pattern formed on the insulating base layer and the insulating cover layer formed on the insulating base layer so as to cover the conductive pattern, includes
a light emitting unit emitting incident light that enters the insulating cover layer and
a light receiving unit receiving reflected light that is reflected from the incident light on the surface of the insulating cover layer, wherein
the light emitting unit includes
a first light emitting portion in a ring state that emits the incident light so that the angle thereof with respect to the surface of the insulating base layer is in the range of 25° or less and
a second light emitting portion in a ring state that emits the incident light so that the angle thereof with respect to the surface of the insulating base layer is in the range of 35 to 65°.

2. The inspection device according to claim 1, wherein the light emitting unit further includes a third light emitting portion in a ring state that emits the incident light so that the angle thereof with respect to the surface of the insulating base layer is in the range of 15 to 45°.

3. The inspection device according to claim 1, wherein the wavelength of the incident light is in the range of 450 to 750 nm.

4. The inspection device according to claim 1, wherein the transmittance of the incident light with respect to the insulating cover layer is in the range of 30% or less.

5. The inspection device according to claim 1, wherein the reflectance of the incident light with respect to the insulating cover layer is in the range of 10 to 30%.

6. A method for producing a wired circuit board comprising the steps of:
forming an insulating base layer;
forming a conductive pattern on the insulating base layer;
forming an insulating cover layer on the insulating base layer so as to cover the conductive pattern; and
inspecting the presence or absence of a foreign object in the insulating cover layer by using an inspection device; wherein
the inspection device includes
a light emitting unit emitting incident light that enters the insulating cover layer and a light receiving unit receiving reflected light that is reflected from the incident light on the surface of the insulating cover layer, wherein
the light emitting unit includes
a first light emitting portion in a ring state that emits the incident light so that the angle thereof with respect to the surface of the insulating base layer is in the range of 25° or less and
a second light emitting portion in a ring state that emits the incident light so that the angle thereof with respect to the surface of the insulating base layer is in the range of 35 to 65°.

* * * * *